(12) United States Patent
Eberhardt et al.

(10) Patent No.: US 6,761,735 B2
(45) Date of Patent: Jul. 13, 2004

(54) HEART VALVE FIXATION PROCESS AND APPARATUS

(75) Inventors: Carol E. Eberhardt, Fullerton, CA (US); Christopher G. Toomes, Orange, CA (US); Mark J Capps, Mission Viejo, CA (US); Billie Millwee, Fullerton, CA (US); Janice Shay, Lake Forest, CA (US); Tom Hessler, Tustin, CA (US); Faisal Kalam, Anaheim, CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/131,979

(22) Filed: Apr. 25, 2002

(65) Prior Publication Data

US 2003/0204251 A1 Oct. 30, 2003

(51) Int. Cl.[7] ................................................. A61F 2/06
(52) U.S. Cl. ........................ 623/2.1; 623/901; 623/915; 8/94.11
(58) Field of Search ................................ 623/2.1, 2.13, 623/11.11, 901, 915, 918, 920, 922; 8/94.11

(56) References Cited

U.S. PATENT DOCUMENTS

| | | | |
|---|---|---|---|
| RE30,912 E | 4/1982 | Hancock | 3/1.5 |
| 4,816,029 A | 3/1989 | Penny, III et al. | 623/2 |
| 4,880,603 A | 11/1989 | Förster | 422/218 |
| 4,976,733 A | 12/1990 | Girardot | 623/11 |
| 5,336,258 A | 8/1994 | Quintero et al. | 623/2 |
| 5,376,110 A | 12/1994 | Tu et al. | 623/1 |
| 5,447,536 A | 9/1995 | Girardot et al. | 8/94.11 |
| 5,716,401 A | 2/1998 | Eberhardt et al. | 623/2 |
| 5,733,339 A | 3/1998 | Girardot et al. | 8/94.33 |
| 5,824,060 A | 10/1998 | Christie et al. | 623/2 |
| 5,824,069 A | 10/1998 | Lemole | 623/2 |
| 5,830,239 A | 11/1998 | Toomes | 8/94.11 |
| 5,855,602 A | 1/1999 | Angell | 623/2 |
| 5,880,242 A | 3/1999 | Hu et al. | 527/200 |
| 5,931,868 A | 8/1999 | Gross | 623/2 |
| 6,074,419 A | 6/2000 | Healy et al. | 623/2.14 |

FOREIGN PATENT DOCUMENTS

WO    WO 02/49681    6/2002

*Primary Examiner*—David H. Willse
*Assistant Examiner*—William H. Matthews
(74) *Attorney, Agent, or Firm*—Thomas G. Berry; Daniel W. Latham

(57) ABSTRACT

A method and apparatus for limiting longitudinal stretch during fixation of a harvested aortic root including valve leaflets and the product produced. The apparatus includes an inflow plug inserted into the inflow section of the aortic root and having an apertured tube or cannula extending through the valve leaflets to an outflow plug inserted into the outflow section of the aortic root. Apertures in the tube are located on either side of the valve leaflets and the tube is coupled to a fluid inlet, preferably located on the outflow plug. The outflow plug is slidable relative to the tube and is provided with an engagement mechanism such as a setscrew for fixing the location of the outflow plug relative to the tube and the inflow plug. After assembly of the aortic root to the apparatus, the fluid inlet is coupled to a source of defined pressure and the root is inflated. The outflow plug is then fixed relative to the tube to define the maximum elongation of the root and fixative is then delivered to the interior of the root via the apertured tube.

9 Claims, 5 Drawing Sheets

HEART VALVE FIXATION PROCESS AND APPARATUS

BACKGROUND OF THE INVENTION

The present invention relates to the production of tissue heart valves generally and more particularly to fixtures for use in conjunction with fixation of valve tissue.

Tissue heart valves may be fabricated by harvesting a mammalian aortic root including the aortic valve and thereafter fixing the harvested aortic root to crosslink the tissue. Thereafter, the aortic root may be trimmed and employed as heart valve for implantation in human beings. The valve may be mounted to a stent or frame, for example as disclosed in U.S. Pat. No. 5,824,069, issued to Lemole, U.S. Pat. No. 4,816,029, issued to Penney, et al., U.S. Pat. No. 5,716,401, issued to Eberhardt, et al. or U.S. Pat. No. RE 30,912, issued to Hancock. Alternatively, the valve may be implanted without an associated stent, as described in U.S. Pat. No. 5,336,258, issued to Quintero, et al or U.S. Pat. No. 6,074,419, issued to Healy, et al.

U.S. Pat. No. 5,824,060 issued to Christie, et al. and incorporated herein by reference in its entirety describes a process for heart valve fixation, in which the harvested aortic root is subjected to a fixative fluid to provide a first differential fluid pressure across the tubular wall of the outflow section of the aortic root and a second differential fluid pressure across the valve leaflets. As disclosed, the inflow and outflow sections of the aortic root are coupled to fluid couplings that are in turn coupled to sources of fixative fluid under pressure. The entire assembly is also placed in fixative fluid during the fixation process.

U.S. Pat. No. 5,830,239 issued to Toomes and incorporated herein by reference in its entirety describes an improvement to the process of the '060 patent, in which only the outflow section of the aortic root is mounted to a fluid coupling and the inflow section of the root is blocked by a plug. The plug is provided with a tube or cannula having an inlet portion extending through the valve leaflets and an outlet opening located in the inflow section of the aortic root, allowing fixative fluid to flow through the valve so that fluid may be applied to both sides of the valve and to the inflow and outflow sections of the aortic root. The fluid coupling is coupled to a source of fixative and the entire assembly is placed in fixative during the fixation process. The process disclosed in the '239 patent substantially simplifies the fixturing process as compared to the '060 patent.

SUMMARY OF THE INVENTION

The present invention is an improvement to the process described in the '239 patent, providing a way to control axial stretch of the aortic root during the fixation process. Because the stretch of the aortic root is controlled, the fixturing system and process of the present invention is intended to produce an increased yield as compared to the process in the '239 patent.

The fixturing system of the present invention resembles that as described in the '239 patent, in that only a single fluid coupling is employed, preferably part of an outflow plug coupled to the outflow section of the aortic root, and in that the inflow section of the aortic root is blocked by an inflow plug. However, in the present invention, the cannula or tube extending from the inflow plug extends through the valve all the way to the outflow plug. The tube smoothly slides into the outflow plug, allowing for adjustment of the relative positions of the inflow and outflow plug. The outflow plug preferably has a setscrew or other mechanism associated therewith for fixing the location of the inflow plug relative to the outflow plug. The tube is provided with a series of holes extending along of the tube and arranged to be located on both sides of the valve leaflets, so that a zero pressure differential across the leaflets can be achieved during fixation.

In use, the outflow section of the aortic root is preferably first coupled to the fluid coupling, which in the preferred embodiment of the invention is part of an outflow plug, around which the outflow section of the aortic root is mounted. The fluid coupling is then coupled to a source of compressed air to close the valve leaflets and a contour ring is placed around the inflow section of the aortic root. The aortic tissue at the end of the inflow section of the aortic root is then folded back over the contour ring and a length of plastic tubing is slid over the tissue and contour ring and is maintained in place, for example, by means of a cable tie. Other mechanisms for restraining the outflow section of the aortic root during fixation may be substituted for the contour ring or the contour ring might, in some embodiments, be attached without prior application of pressure to close the valve leaflets.

The apertured tube or cannula and the attached inflow plug are then inserted into the aortic root with the tube passing through the valve leaflets and engaging the fluid coupling. The inflow plug attached to the tube is located within the plastic tubing and attached to it by means of cable ties or the like, compressing the tubing around the inflow plug. The fluid coupling is then again attached to a source of compressed air, which is used to inflate the aortic root to a desired pressure and the setscrew is employed to fix the outflow plug to the tube, correspondingly stabilizing the relative location of the inflow and outflow sections of the aortic root and preventing excessive longitudinal stressing during fixation. The assembly is then moved to a fixative bath where the outflow plug is coupled to a source of fixative under pressure, and the assembly is placed into the fixative bath during the fixation process. On completion of fixation, the aortic root is removed and trimmed and may thereafter be mounted to an associated heart valve stent.

DESCRIPTION OF THE PREFERRED EMBODIMENTS

Figure 1:
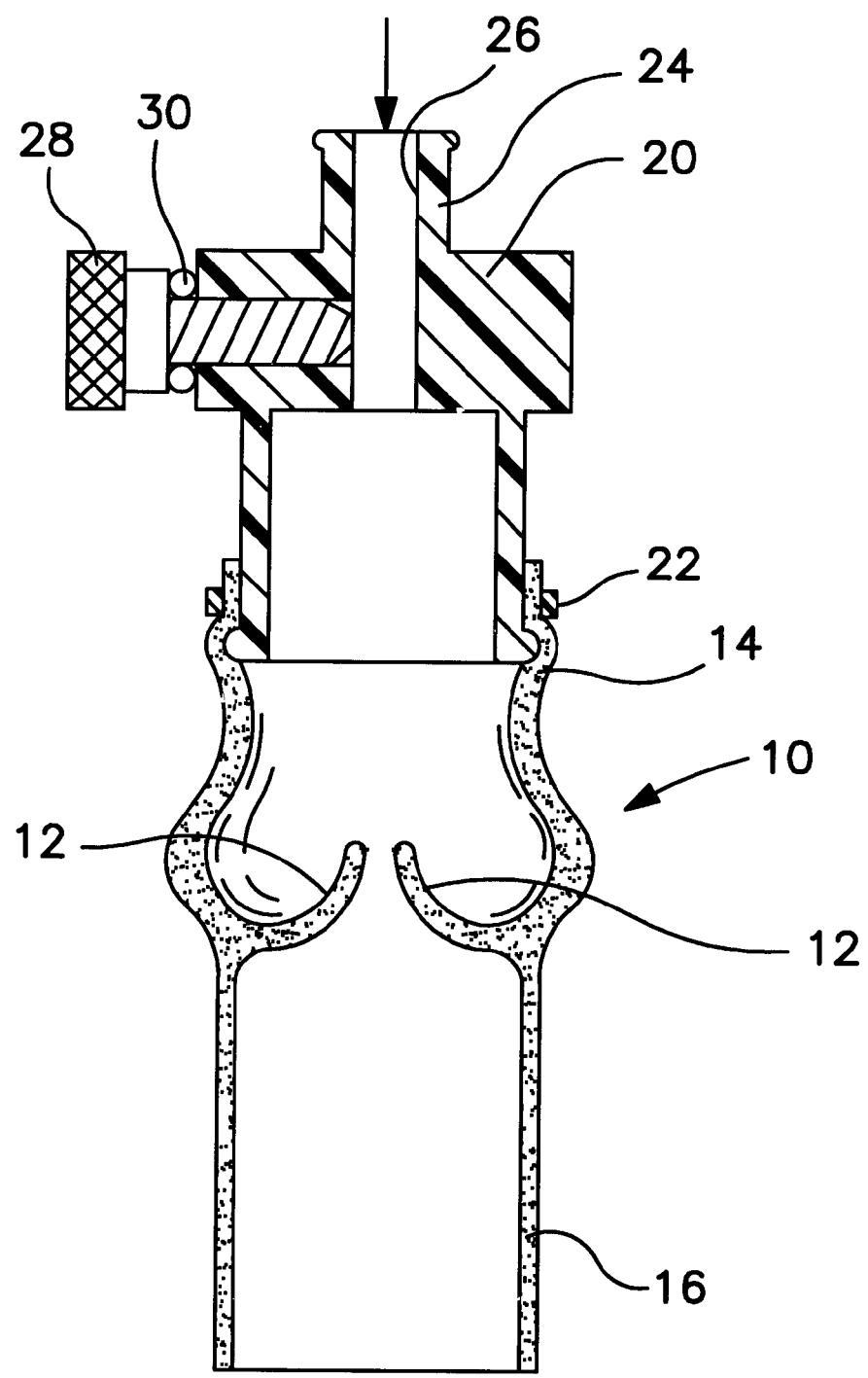
FIG. 1 shows a cross section of a harvested porcine aortic root mounted to the outflow plug of the present invention.

FIG. 1 is a cut away view illustrating a harvested porcine aortic root 10 mounted to outflow plug 20. The aortic root includes the leaflets 12 of the aortic valve, an outflow section 14 and an inflow section 16. In the fixation method of the present invention, the outflow section 14 is first mounted to the outflow plug 20 by inserting the plug 20 into the outflow section 14 and compressing the outflow section around the plug 20 by means of a cable tie 22 or the like.

The outflow plug 20 is provided with a fluid coupling 24, including a fluid inlet lumen 26. Also included in outflow plug 20 are a threaded setscrew 28 and an o-ring 30. As discussed above, the setscrew functions to lock the position of the outflow plug 20 relative to the tube or cannula and the attached inflow plug (not illustrated). As such, the screw 28 is sized so that when its end is engaged with the tube extending through the input passage 26, O-ring 30 will be compressed to provide a fluid seal to prevent leakage of fixative or air, along the threads of the screw 28.

Figure 2:
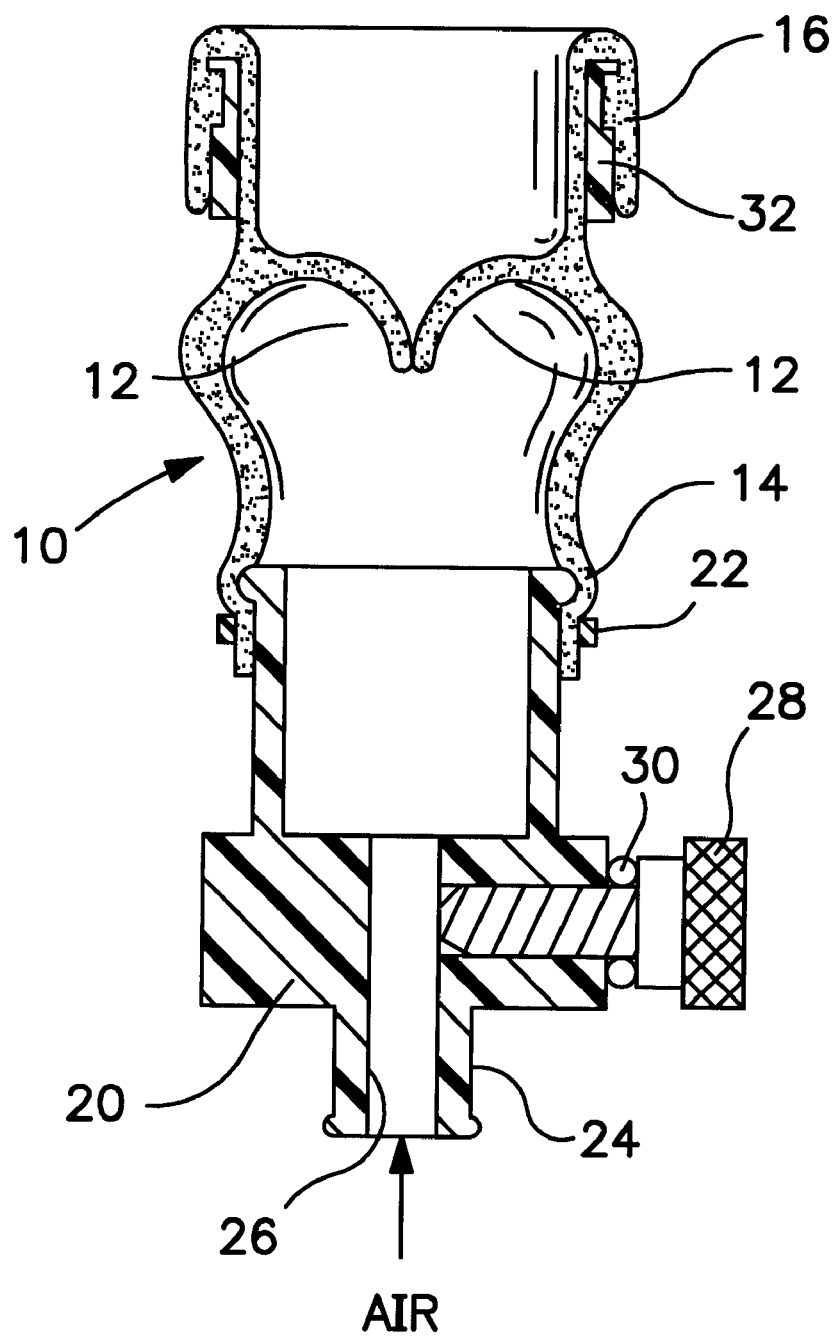
FIG. 2 shows the aortic root and outflow plug of FIG. 1 inverted so that the outflow plug may be coupled to a source of compressed air to close the valve leaflets and allow placement of the contour ring.

FIG. 2 is a cut away view of the assembly of FIG. 1, inverted to allow attachment to a source of compressed air via fluid coupling 24. Other numbered items correspond to identically numbered items in FIG. 1. The process according to the present invention continues from the previous steps illustrated in FIG. 1 as follows. Fluid coupling 24 is coupled to a source of compressed air at approximately two inches $H_2O$ of pressure. This serves to close the leaflets 12 of the aortic valve, maintaining the aortic root in a position in which the leaflets properly coapt. Contour ring 32 is then slid over the inflow section 16 of the aortic root 10, and the end of the inflow section is folded over the contour ring 32. As described in the above cited '239 et al patent, contour ring 32 serves to maintain the configuration of the aortic root in the vicinity of the leaflet bases in an appropriate configuration to assure valve coaption after fixation.

Figure 3:
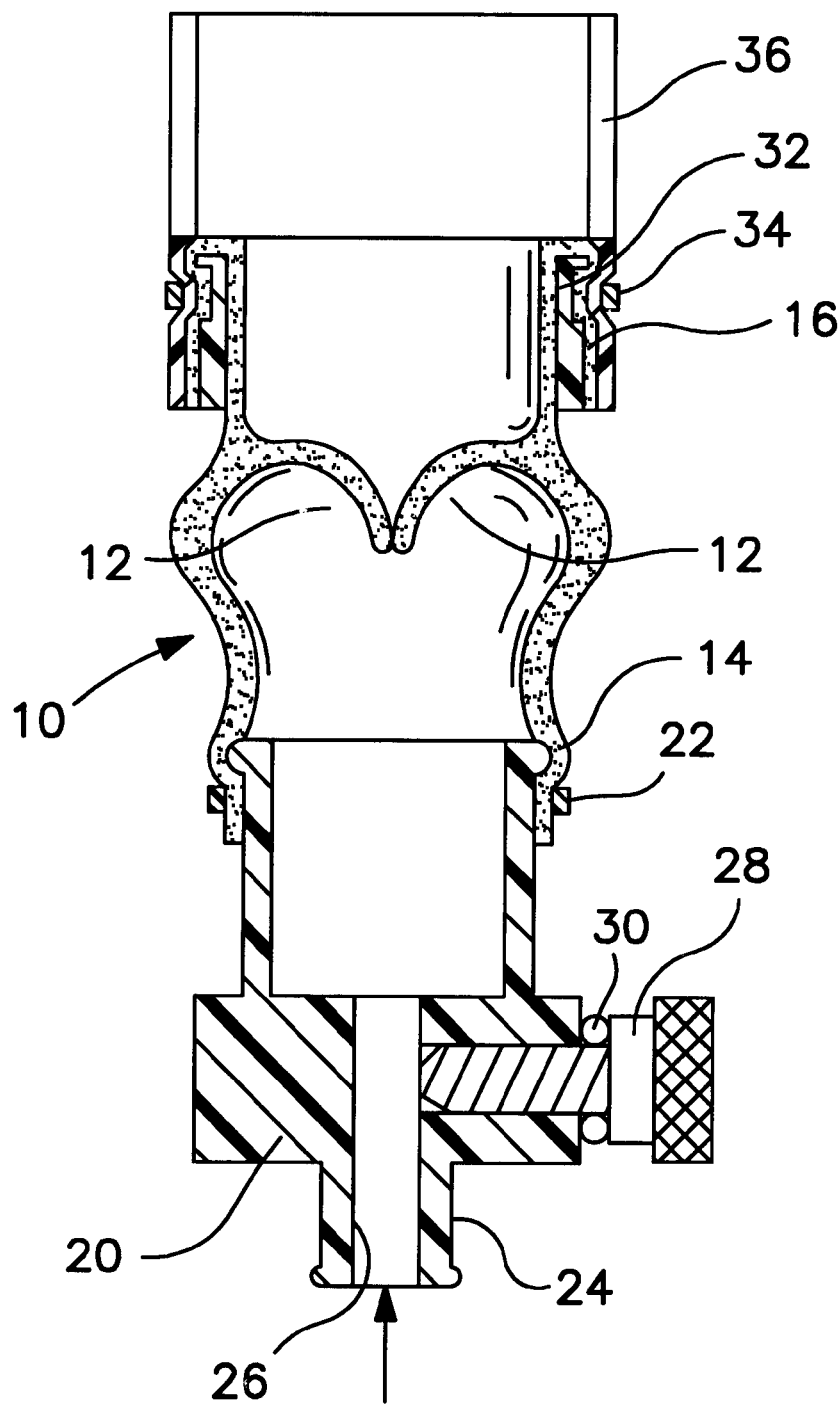
FIG. 3 shows the assembly of FIG. 2 after addition of a length of plastic tubing, mounted around the contour ring and inflow section of the aortic root.

FIG. 3 illustrates the apparatus in FIG. 2, during the next steps of the process according to the present invention. All numbered items correspond to identically numbered items if FIG. 2. After placement of the contour ring 32 around the inflow section 16 of the aortic root 10, a plastic tube 36 which can be fabricated, for example, of silicone rubber is slid over the inflow section 16 and the contour ring 32 and is maintained in place by means of a cable tie 34 or the like as illustrated. Silicone tube 36 will serve to mount the inflow plug and associated tube, as discussed below.

Figure 4:
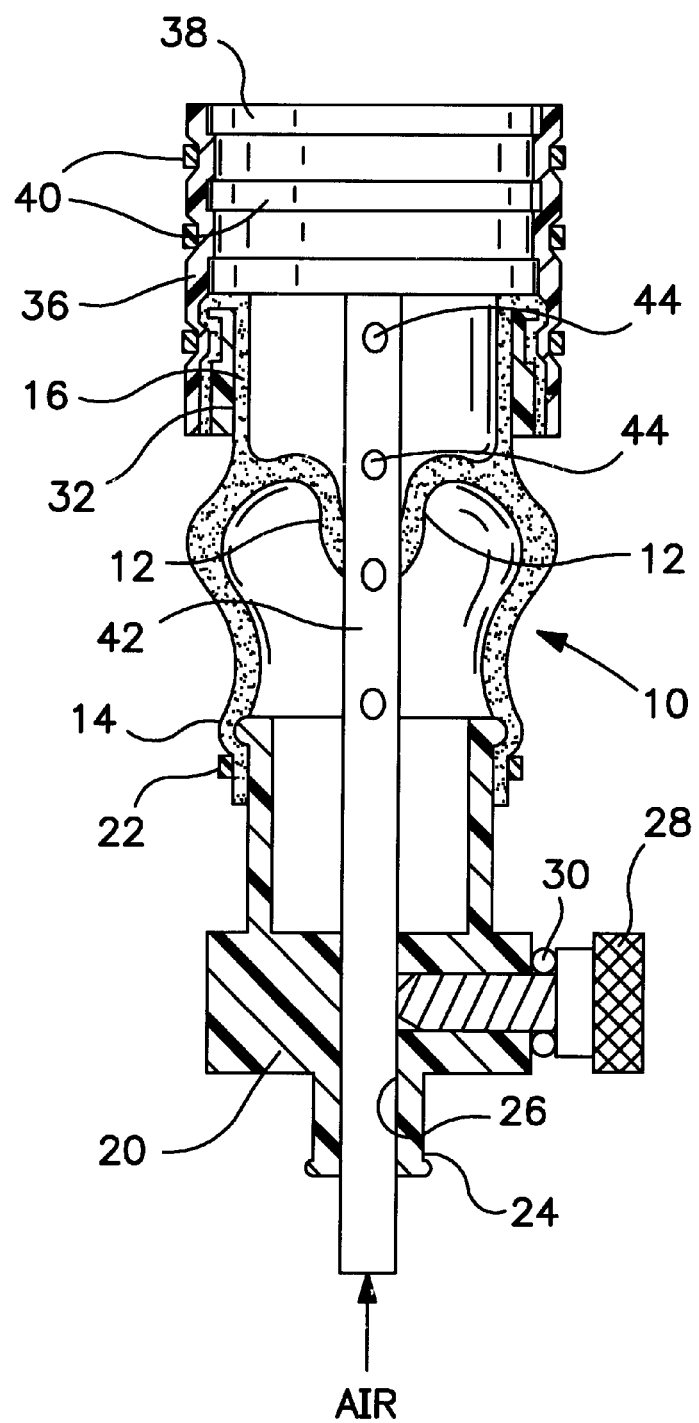
FIG. 4 shows the assembly of FIG. 3 to which the inflow plug and associated tube have been mounted.

FIG. 4 illustrates the next step in the process according to the invention, and includes the apparatus illustrated in FIG. 3 above. Numbered components correspond to identically numbered components in FIG. 3 above.

Inflow plug 38 and associated tube 42 have been added to the assembly of FIG. 3 above. The inflow plug 38 is sealed within plastic tube 36 by means of one or more cable ties 40 or the like. The plug thus effectively seals the inflow section of the aortic root 10 against leakage. Apertured tube 42, mounted to inflow plug 38, extends through the aortic valve leaflets 12, and outward through the fluid inlet lumen 26 in fluid coupling 24. Fluid inlet 24 is then coupled to a source of compressed air, preferably at about 10 plus or minus 1 inches $H_2O$. The pressurized air is delivered to the interior of the aortic root in both the outflow and inflow sections, primarily by means of holes 44 in tube 42. The air pressure serves to inflate the aortic root to a desired, but limited degree. During inflation, tube 42 is free to slide within the internal lumen 26 of fluid inlet 24 to an optimal position for fixation. The inlet and outflow plugs 38, 20 and the attached aortic root 10 are now in the desired configuration for the fixation process.

After inflation of the aortic root, setscrew 28 is tightened against tube 42 to lock it in position relative to the outflow plug 20 and fluid coupling 24. O-ring 30 is concurrently compressed to seal against fluid losses during fixation that might otherwise occur around the threads of screw 28. The assembly is now ready to be placed in the fixative bath and attached to a source of fixative. It has been determined that allowing inflation of the valve to determine the spacing of the inflow and outflow plugs provides for a procedure which produces preserved porcine aortic roots without undue longitudinal stretching, improving the yield of the process.

Figure 5:
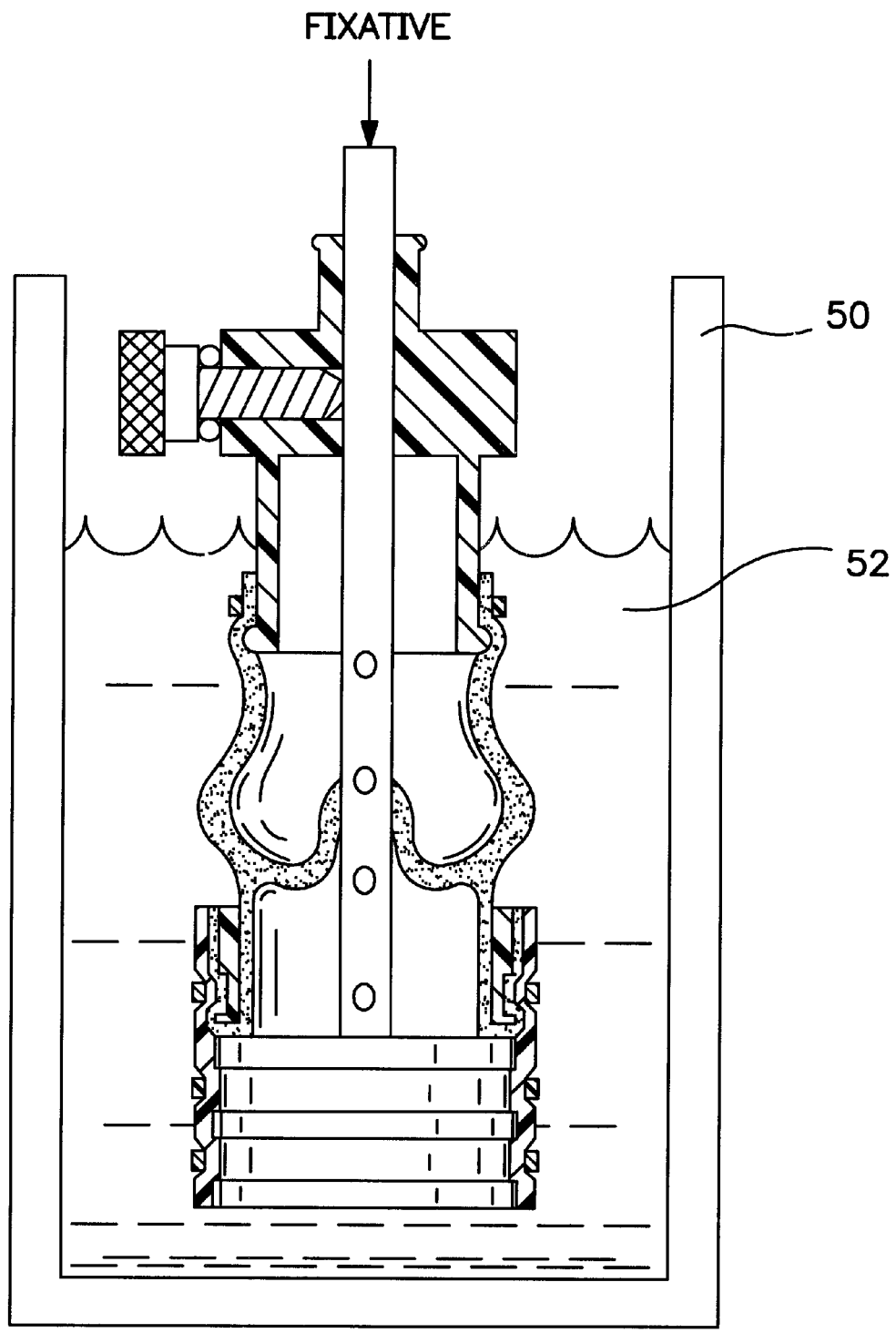
FIG. 5 illustrates the assembly of FIG. 4 mounted in a fixative bath.

FIG. 5 is a cut away view illustrating the fixation portion of the process according to the present invention. In this view, the assembly illustrated in FIG. 4 is inverted and placed in a fixative bath 50, containing fixative 52 which may be, for example, a 0.2% aqueous solution of gluteraldehyde. Other fluid fixatives (liquid or gaseous), as disclosed in U.S. Pat. No. 5,880,242, issued to Hu, et al., U.S. Pat. No. 5,733,339, issued to Girardot, et al., U.S. Pat. No. 5,376,110, issued to Tu, et al., U.S. Pat. No. 5,447,536, issued to Girardot, et al., U.S. Pat. No. 5,931,868, issued to Gross, et al. or U.S. Pat. No. 4,880,603, issued to Jaffe, all incorporated herein by reference in their entireties, may also be employed in conjunction with the method of the present invention. The fluid inlet 24 is coupled to a source of fixative under pressure, for example, the same as fixative 52, but under pressure. The fixative is delivered to the interior of the aortic root via the holes 44 in tube 42. The assembly remains in the fixative bath with pressurized fixative applied via the fluid coupling 24 until fixation is complete. Fixation times will vary as a function of the pressures and fixatives employed. Anti-calcification treatments, for example using alpha-aminooleic acid as described in U.S. Pat. No. 4,976,733, issued to Girardot, et al. and incorporated herein by reference in its entirety, may also be employed.

In a preferred embodiment of the invention using a porcine aortic root, the pressure the fixative solution provided via the fluid coupling 24 is adjusted to provide a pressure drop across the walls of the aortic root of about 40 mm Hg. However, as described in the '060 and '239 patents cited above, the pressure drop may be substantially higher or lower, e.g. 20–120 mm Hg. The desired pressure drop may also vary as a function of the species from which the aortic root was harvested. Because the fluid is delivered at equal pressure to both sides of the aortic valve leaflets 24, there is effectively a zero pressure drop across the valve leaflets. The pressure drop across the walls of the aortic root is determined by the difference between the inlet pressure at fluid inlet 24 and the pressure of the fixative solution 52 in the fixative bath 50. While FIG. 5 illustrates a single fixture and aortic root assembly located in a fixation tank, it should be understood that in commercial embodiments of the present invention, multiple such assemblies will be coupled to piccolo tubes as described in the above-cited '239 patent, and simultaneously fixed within a larger fixative bath.

It should be noted that while the disclosed embodiment employs a setscrew to fix the tube to the fluid coupling, other mechanisms such as clamps, collects, pins, cams, detects or other devices may be substituted. Further, while in the embodiment as described, the pressure differential across the walls of the aortic root is kept generally constant during the fixation process, pulsatile or varying pressure may in some cases be employed. In addition, while in the preferred embodiment, the fluid coupling is mounted to the inflow plug and extends through the outflow plug, it is possible that a reversal of these elements so that the fluid coupling is associated with the. Finally, while inflation of the aortic root to establish the desired spacing of the inflow and outflow plugs, it is believed that the invention might still be usefully practiced in embodiments in which some other method, e.g. mechanically stretching the root to a desired length or tension, is used to determine the desired spacing. As such, the above-disclosed embodiment should be considered as exemplary, rather than limiting in conjunction with the claims that follow.

What is claimed is:

1. A method for fixing a harvested aortic root having an inflow section, an outflow section and valve leaflets, comprising:

sealing the inflow and outflow sections of the aortic root to first and second plugs;

placing an apertured tube through the aortic root such that the tube passes through the leaflets and extends from the first plug to the second plug;

fixing the tube with respect to the first and second plugs such that the tube at least partially supports the first and second plugs in a desired relative position; and delivering fixative to the aortic root via the apertured tube.

2. A method according to claim 1, wherein fixing the tube comprises tightening a setscrew against the tube.

3. A method according to claim 1, further comprising inflating the aortic root to a desired pressure, prior to fixing the tube.

4. A method according to claims 1, 2 or 3, further comprising inflating the aortic root to cause the leaflets to close, prior to sealing the inflow section of the aortic root and, with the leaflets closed, mounting a ring around the inflow section of the aortic root.

5. A method according to claims 1, 2, or 3, further comprising placing the aortic root in fixative during delivery of the fixative to the aortic root via the apertured tube.

6. Apparatus for use in fixing a harvested aortic root having an inflow section, an outflow section and valve leaflets, comprising:

first and second plugs, each sized to fit within one of the inflow and outflow sections of the aortic root;

an apertured tube mounted to the second plug, sized to extend though the valve leaflets and having a length sufficient to extend through the aortic root from the inflow section to the outflow section, engagable with and slidable relative to the first plug; and a fluid inlet coupled to the apertured tube.

7. Apparatus according to claim 6, wherein the first plug comprises an engagement mechanism operable to fix the tube in position relative to the first plug.

8. Apparatus according to claim 7, wherein the engagement mechanism comprises a setscrew rotatable into engagement with the apertured tube.

9. Apparatus according to claims 6, 7, or 8, wherein a fluid coupling is located on the first plug and wherein the apertured tube extends into the fluid inlet.

* * * * *